(12) United States Patent
Jones et al.

(10) Patent No.: US 6,844,235 B1
(45) Date of Patent: Jan. 18, 2005

(54) RETICLE REPEATER MONITOR WAFER AND METHOD FOR VERIFYING RETICLES

(75) Inventors: Christopher M. Jones, San Francisco, CA (US); Mira Ben-Tzur, Sunnyvale, CA (US); Allen Fung, San Francisco, CA (US)

(73) Assignee: Cypress Semiconductor Corporation, San Jose, CA (US)

( * ) Notice: Subject to any disclaimer, the term of this patent is extended or adjusted under 35 U.S.C. 154(b) by 85 days.

(21) Appl. No.: 09/920,374

(22) Filed: Jul. 31, 2001

(51) Int. Cl.$^7$ .................. H01L 21/76; H01L 21/301; H01L 21/44; H01L 21/461
(52) U.S. Cl. .................. 438/401; 438/462; 438/612; 438/653; 438/656; 438/720; 438/945
(58) Field of Search .................. 438/401, 462, 438/688, 720, 785, 945, 975, 612, 653, 656, 107, 109

(56) References Cited

U.S. PATENT DOCUMENTS

| | | | | |
|---|---|---|---|---|
| 5,707,883 A | * | 1/1998 | Tabara | 438/297 |
| 5,854,503 A | * | 12/1998 | Hsueh et al. | 257/347 |
| 5,985,693 A | * | 11/1999 | Leedy | 438/107 |
| 5,998,300 A | * | 12/1999 | Tabara | 438/700 |
| 6,174,820 B1 | * | 1/2001 | Habermehl et al. | 438/745 |
| 6,294,909 B1 | * | 9/2001 | Leedy | 324/207.17 |
| 6,303,447 B1 | * | 10/2001 | Chhagan et al. | 438/299 |
| 6,303,459 B1 | * | 10/2001 | Chen | 438/401 |
| 6,420,766 B1 | * | 7/2002 | Brown et al. | 257/401 |

* cited by examiner

*Primary Examiner*—Long Pham
*Assistant Examiner*—Shrinivas H. Rao
(74) *Attorney, Agent, or Firm*—Bradley T. Sako

(57) ABSTRACT

According to one embodiment, verifying a reticle may include patterning an inspected layer (102-2) according to a reticle pattern, depositing a contrast enhancing layer (104-0) on a patterned layer (102-2), and inspecting a reticle patterned formed in the inspected layer (102-2).

20 Claims, 4 Drawing Sheets

RETICLE REPEATER MONITOR WAFER AND METHOD FOR VERIFYING RETICLES

TECHNICAL FIELD

The present invention relates generally to semiconductor processing and more particularly to the verification of photomasks used in semiconductor processing.

BACKGROUND OF THE INVENTION

Integrated circuits are typically manufactured by forming and/or altering multiple layers on a semiconductor wafer. Particular steps may include depositing a layer, forming a pattern over the layer, and etching the pattern. Such steps may form various structures, including but not limited to trenches in a substrate, a transistor gate layer from a layer of polycrystalline silicon (polysilicon), contacts to a substrate/gate, various interconnect layers, and vias between interconnect layers.

One common method of forming patterns on a layer includes photolithography in conjunction with a photoresist layer. More particularly, a layer of photoresist may be deposited over a layer and patterned formed in the layer by shining light through a pattern.

Many current manufacturing processes photolithography steps are accomplished with a machine called a "stepper." A stepper typically includes a light source and a reticle. A reticle can be designed to include (or ultimately) a desired pattern in an underlying layer of photoresist. A reticle may include the pattern for one die, or multiple dies.

In operation, a layer of photoresist can be deposited (e.g., spun) on the surface of a layer. A stepper may then "step" across the entire wafer, essentially developing the reticle pattern in the underlying photoresist layer. Undeveloped portions of a pattern may then be removed by a solvent, or the like.

It follows that the proper manufacturing of a semiconductor device can rely on assuming that the pattern contained in a reticle is good (i.e., ultimately produces a desired pattern in an underlying layer). Unfortunately, this is not always the case.

Various factors can contribute to a defect in a reticle. As but a few of the many possible examples, such defects may arise when a reticle is manufactured (a particle, unwanted spot, etc.), or may be inherent in a database that produces a reticle pattern (corrupted database, etc.).

Thus, prior to utilizing a new reticle in a manufacturing process, it is desirable to first inspect a reticle to ensure its pattern is valid.

Various factors can contribute to the importance of "proving" a reticle (ensuring its pattern is valid). A semiconductor device manufacturer often contracts a vendor to make a reticle. Therefore, in many cases, a manufacturer will not know if a reticle is good until it is received and inspected. Second, because reticle manufacturing is outsourced, if a reticle has a defect, there may be some turnaround time before a new reticle can be generated correcting any defects (of course the new reticle will also have to be inspected).

Various conventional methods for reticle inspection are known. As but one example, a reticle may inspected with a database-to-reticle inspection. Alternatively, a chip-to-chip comparison can be performed. A database-to-reticle inspection can prove the integrity of the photomask data, while the chip-to-chip comparison may be useful in detecting random defects or defocusing issues associated with the reticle fabrication. Such inspections may be performed in an automated fashion with inspection machines such as a KLA351 manufacture by KLA-Tencor Corporation, or an Orbit RT-8000 manufactured by Orbotech, Ltd., or the like.

Due to the very small feature sizes, and very large patterns of an integrated circuit layer, it is desirable to utilize an inspection machine to prove a reticle. Such inspection machines typically require a minimum contrast between edges of a pattern and open (i.e., non-patterned) areas.

A conventional method of inspecting a reticle with a patterned wafer will now be described with reference to FIGS. 3A–3E. FIGS. 3A–3E shows various steps in boxes on the right, with example illustrations of a method on the left.

Referring to FIG. 3A, a wafer can be prepared for a resist verification flow. In FIG. 3B, a layer of photoresist 304 can be formed on the wafer 302, by spinning, or the like. Processing can continue as shown in FIG. 3C with a reticle 308 selectively exposing portions of a resist covered wafer to a light source, or the like. A FIG. 3D shows photoresist pattern 310 which may be formed after a photoresist layer has been developed, and undeveloped portions have been removed. In this way, a pattern in a reticle can be transferred to a layer of photoresist.

Finally, a wafer can be inspected in FIG. 3E for pattern defects and anomalies.

A method according to FIGS. 3A–3E may have several drawbacks. Because a pattern may be formed directly on a wafer, there can be little contrast between the exposed and unexposed areas of the wafer. This can make inspection difficult. In addition, the various exposure parameters used to form a layer in photoresist may be different from those used to form an actual semiconductor device. In particular, in production (the manufacturing of a device), a patterned layer may be higher from the surface, resulting a patterned being developed in a different focal plane. Still further, the amount of light (or other developing form of radiation) may differ between an inspection pattern, and that used in production. Consequently, conventional inspection processes that transfer a pattern into a photoresist may not adequately reproduce a pattern or provide sufficient contrast in a pattern.

A finished conventional inspection wafer may have further drawbacks. A pattern of photoresist formed on a wafer surface may not provide sufficient contrast to enable an inspection machine to automatically align a wafer. This can be time consuming and add a manually intensive task to an inspection method.

Yet another drawback to a conventional inspection process, such as that shown in FIGS. 3A to 3E, can be the difficulty in examining various features at a high magnification. More particularly, many features may have to be examined under a scanning electron microscope (SEM). Unfortunately, photoresist may have a tendency to charge under an electron beam. While low energy electron beam systems may be capable of reducing charging, such systems can be expensive and do not always completely eliminate charging. Charging can lead to periodic flashes, and/or bright spots that may obstruct or distort a feature under examination, thereby preventing accurate verification of a feature and or measurement of a defect.

Another conventional method, as noted above, can be an inspection following a short-loop flow. A short-loop flow is so named because a wafer is taken through only a portion of the chip processing flow. While this may add complexity to a flow such as that shown in FIGS. 3A–3E, it can also use recipes, equipment, and/or lithography step of an existing process. Thus, exposure and focus settings of a short loop inspection wafer can be essentially the same as a production wafer. This is in contrast to the example of FIGS. 3A to 3E, where a photoresist may be underexposed or developed in a different focal plane.

Short-loop flows may also have drawbacks, however. A short-loop flow adds more complexity to a process. Still further, each additional process step in a short loop may introduce defects not associated with, or resulting from, a reticle defect. As but one example, chemical-mechanical-polishing (CMP) may increase the number of particles on wafer. This can distract the inspection system from detecting true reticle related defects.

In light of the above, it would be desirable to arrive at some way of verifying reticles that does not suffer from the various drawbacks of conventional approaches, such as those noted above.

SUMMARY OF THE INVENTION

According to the disclosed embodiments, a method of verifying reticles may include forming an inspected layer on a semiconductor substrate that may contain a reticle pattern. An inspected layer may be a non-resist layer. A conformal conductive layer may then be deposited over an inspected layer. An inspected layer may then be inspected to determine if a corresponding reticle pattern has defects or not.

According to one aspect of the embodiments, a conformal layer may be a conductive material. Such a conductive layer may comprise titanium, titanium nitride, or some combination thereof.

According to one aspect of the embodiments, a conformal layer may be a conductive conformal layer.

According to another aspect of the embodiments, an inspected pattern may include various features. Such features may have a minimum size L. A conformal conductive layer may have a thickness that is ½L or less.

According to another aspect of the embodiments, a conformal conductive layer may have a thickness less than 1000 Å.

According to another aspect of the embodiments, an inspected layer may include silicon oxide. More particularly, an inspected layer may include undoped silicon dioxide formed on a layer of phosphosilicate glass.

According to another aspect of the embodiments, an inspected layer may have a thickness greater than 2500 Å.

According to another aspect of the embodiments, an inspected layer may be automatically inspected with pattern inspection equipment.

According to another aspect of the embodiments, an inspected layer may be automatically aligned within an inspected pattern.

DETAILED DESCRIPTION OF THE EMBODIMENTS

Various embodiments will now be discussed in conjunction with a number of figures. The various embodiments show methods for inspecting a reticle to determine if the reticle includes defect.

Figure 1A:
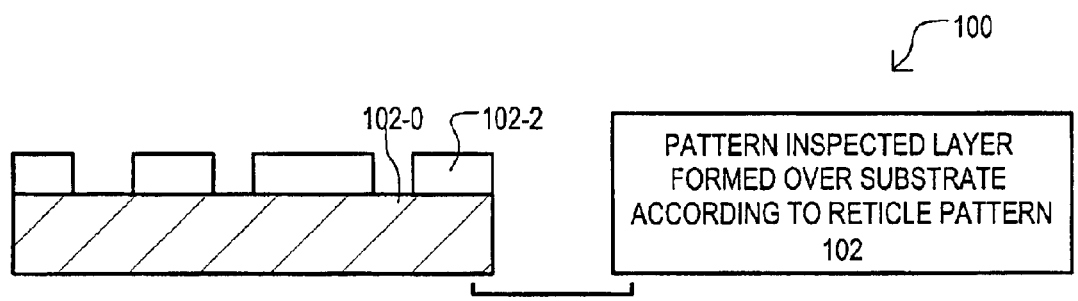
FIGS. 1A to 1C show a method according to a first embodiment.
Figure 1B:
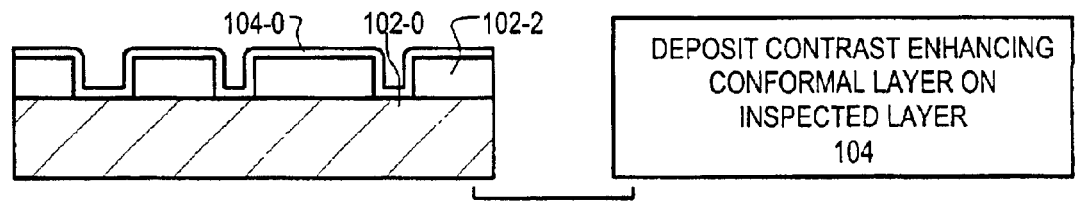
Figure 1C:
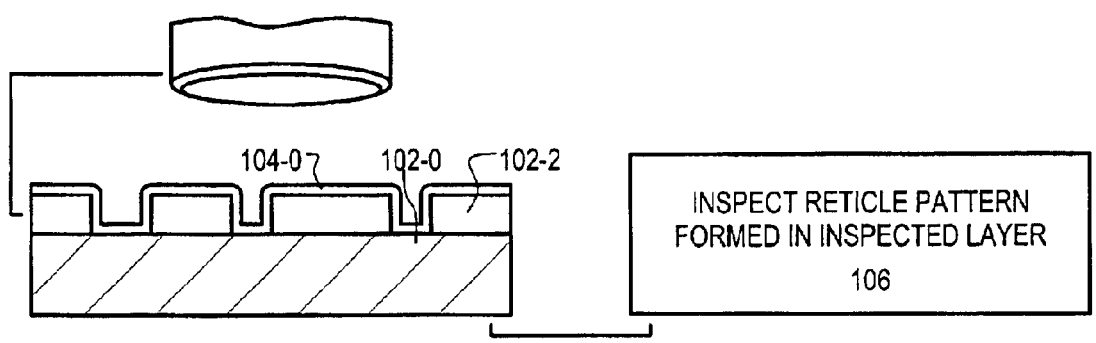

Referring now to FIGS. 1A–1C, a reticle inspection method according to one embodiment is designated by the general reference character 100, and is shown as a series of steps with corresponding side cross sectional views.

As shown in FIG. 1A, a method according to one embodiment may include patterning a layer formed on a substrate according to a reticle pattern (step 102). As but one example, a step 102 may include patterning an inspected layer 102-2 formed on a wafer substrate 102-0. An inspected layer 102-2 may include one or more materials formed on a wafer substrate 102-0 that may be patterned to contain features that reflect a reticle pattern. Thus, an inspection of an inspected layer 102-2 can reveal defects in a reticle. An inspected layer 102-2 may be formed according to various photolithographic techniques, including but not limited to those described above in the Background of the Invention.

Unlike conventional approaches, that may inspect a resist pattern, according to the embodiment of FIGS. 1A–1C a non-resist pattern may be inspected. This may also be in contrast to short loop approaches that may include intermediate patterned layers between an inspected layer and a wafer substrate.

A method 100 may further include depositing a contrast enhancing conformal layer over an inspected layer (step 104). As shown in FIG. 1B, a conformal layer 104-0 may cover features of a pattern formed in an inspected layer 102-2. For example, if a patterned layer includes holes formed within, a conformal layer 104-0 may extend into such holes and adhere to the sides of such holes.

A conformal layer 104-0 may also be contrast enhancing with respect to an inspection method and/or tool. That is, following the formation of a conformal layer 104-0, there may be greater contrast between pattern feature edges and other portions of an inspected layer 102-2 than an inspected layer 104-0 alone.

A method may also include inspecting a reticle pattern formed in an inspected layer (step 106). As noted above, inspection methods/tools may include, but are not limited to, the various examples described above: manual optical inspection or inspection by scanning electron microscope, or various automatic inspection methods such as database-to-reticle and/or chip-to-chip. A conformal layer 104-0 may increase contrast to improve anyone or all of the above-mentioned methods.

It is noted that an arrangement such as that shown in FIGS. 1A–1C may include advantages over conventional approaches. In particular, an inspection layer can be patterned according to photolithographic techniques. In such a case, a resist pattern may be formed on an inspection layer, and not upon a wafer surface itself. This may provide a more advantageous focal plane. That is, a focal plane for developing a resist pattern may be higher from a wafer surface. In some cases photolithographic steps of an existing manufacturing process may be used to pattern an inspection layer. In this way, the complexity of an inspection process may be reduced over approaches that may require specific photolithographic settings that set a focal plane closer to a wafer surface.

As will be noted in more detail below, a conformal layer that includes one or more layers of a conductive layer may provide improved SEM imaging by preventing charging that may occur when examining a pattern of photoresist.

Having described one embodiment of a method for inspecting a reticle, a more detailed embodiment will now be described with reference to FIGS. 2A–2G.

Referring now to FIGS. 2A–2G, a reticle inspection method according to a second embodiment is designated by the general reference character 200, and is shown as a series of steps with corresponding side cross sectional views.

Figure 2A:
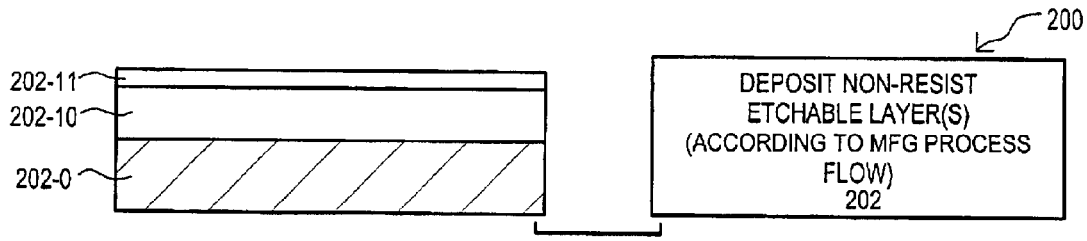
FIGS. 2A to 2F show a method according to a second embodiment.

Referring to FIG. 2A, a method may begin by depositing one or more non-resist etchable layers (step 202). In the particular example, two etchable layers (202-10 and 202-11) may be formed on a wafer substrate 202-0. Etchable layers (202-10 and 202-11) may preferably be formed according to an existing manufacturing process. In one embodiment, one or more etchable layers may be formed according to existing manufacturing steps. More particularly, such a layer(s) may be formed from an interlayer dielectric that may be used to separate a conductive layer from a substrate or another conductive layer in an integrated circuit.

In one embodiment, etchable layers (202-10 and 202-11) may comprise like materials enabling a single etching to form a pattern through both. More particularly, both layers may comprise silicon dioxide. Even more particularly, an etchable layer 202-10 may comprise phosphosilicate glass (PSG), while an etchable layer 202-11 may comprise silicon dioxide formed by the decomposition of tetraethylorthosilicate (TEOS).

In one embodiment, etchable layers (202-10 and 202-11) may comprise like materials enabling a single etching to form a pattern through both. More particularly, both layers may comprise silicon dioxide. Even more particularly, an etchable layer 202-10 may comprise phosphosilicate glass (PSG), while an etchable layer 202-11 may comprise silicon dioxide formed by the decomposition of tetraethylorthosilicate (TEOS).

One or more etchable layers in a step 202 may have a particular thickness. As but one example, etchable layer(s) may have a thickness greater than about 500 Å, preferably greater than about 2000 Å, even more preferably greater than about 5000 Å. In one very particular example, an etchable layer 202-10 may comprise 6000 Å of phosphosilicate glass (PSG) and an etchable layer 202-11 may comprise 2000 Å of TEOS silicon oxide.

Figure 2B:
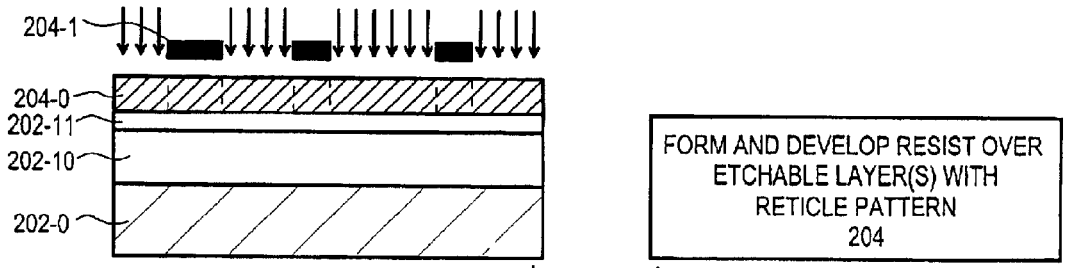

Referring to FIG. 2B, a method 200 may further include forming and developing a layer of resist over etchable layers with a reticle pattern (step 204). A step 204 may initially form a reticle pattern within a layer of resist. Such a pattern may then be transferred underlying etchable layers. A step 204 may include depositing and spinning a resist layer 204-0 on an etchable layers (202-11). A reticle pattern 204-1 that is to be verified may be used to selectively expose a resist layer 204-0 to a radiation source, such as a particular frequency (or frequencies of light). Of course various alternate lithographic techniques may also be employed to transfer a reticle pattern onto a layer of resist, including but not limited the examples noted in the Background of the Invention.

Figure 2C:
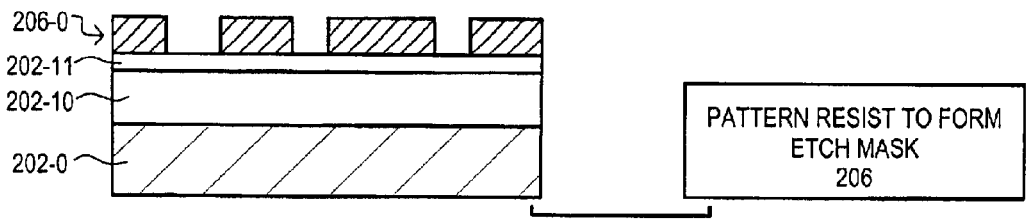

Referring to FIG. 2C, following exposure, a resist layer may be patterned to form an etch mask (step 206). One example of a resulting resist layer etch mask is shown as item 206-0 in FIG. 2C. Such a step may include, as but one example, rinsing away unexposed portions of a resist layer 204-0 with a solvent or the like. In this way, a reticle pattern may be transferred to a resist layer.

Figure 2D:
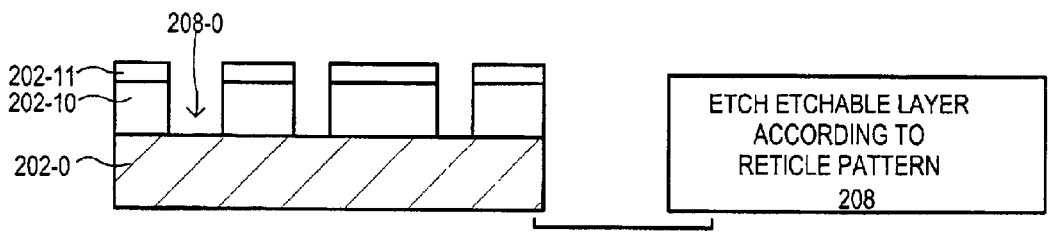

Referring to FIG. 2D, a method 200 may continue by etching an etchable layer(s) according to a reticle pattern (step 208). A step 208 may include anisotropic etching, more particularly reactive ion etching (RIE). While a step 208 may include a single etching step, such a step may also include multiple etching steps. As but one example, a first etch may etch essentially only an etchable layer 202-11 of undoped silicon dioxide to form a "hard" etch mask. A resist etch mask may then be removed. An etchable layer 202-11 of doped silicon dioxide may then be etched with the hard etch mask of undoped silicon dioxide. In this way, a pattern transferred to a resist layer may be transferred to one or more etchable layers.

A step 208 may result in features (one of which is shown as item 208-0) being formed in one or more etchable layers (202-10 or 202-11). Such features can reflect a reticle pattern that may then be examined.

Figure 2E:
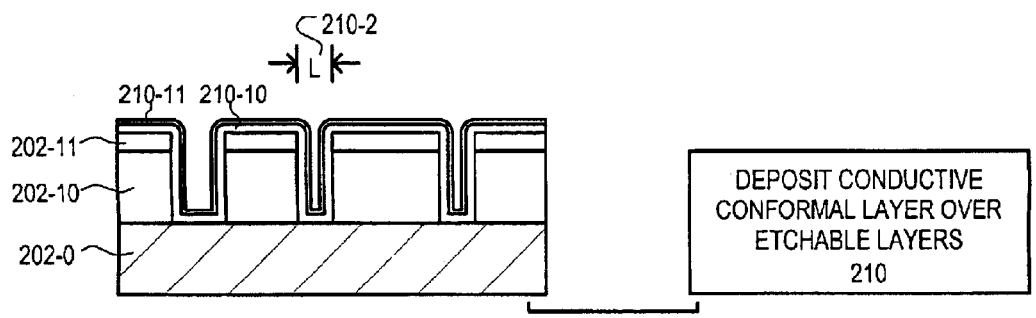
Figure 2F:
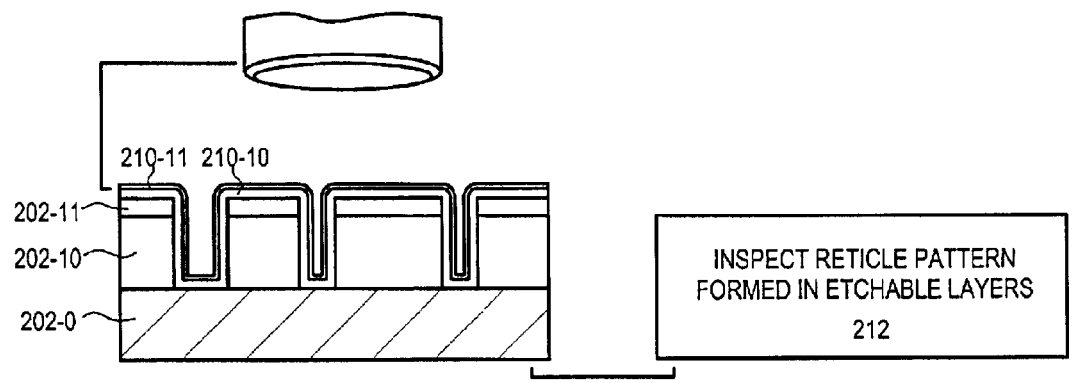
Figure 3A:
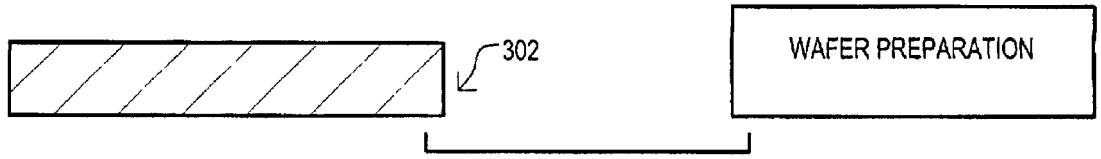
FIGS. 3A to 3E show a conventional method of inspecting a reticle.
Figure 3B:
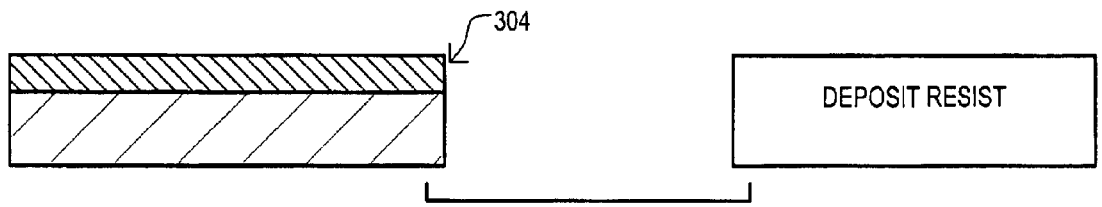
Figure 3C:
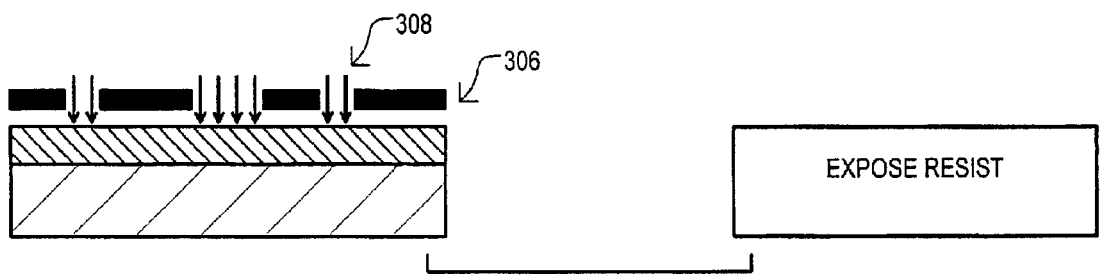
Figure 3D:
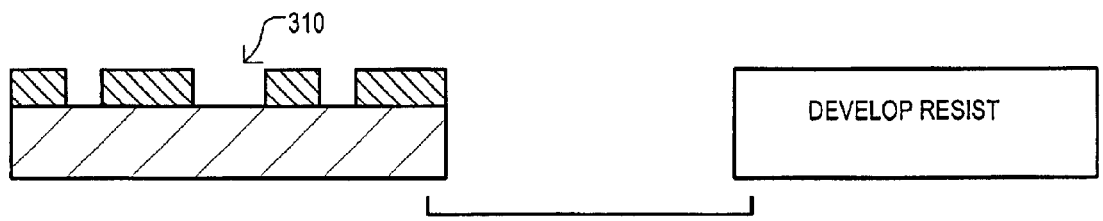
Figure 3E:
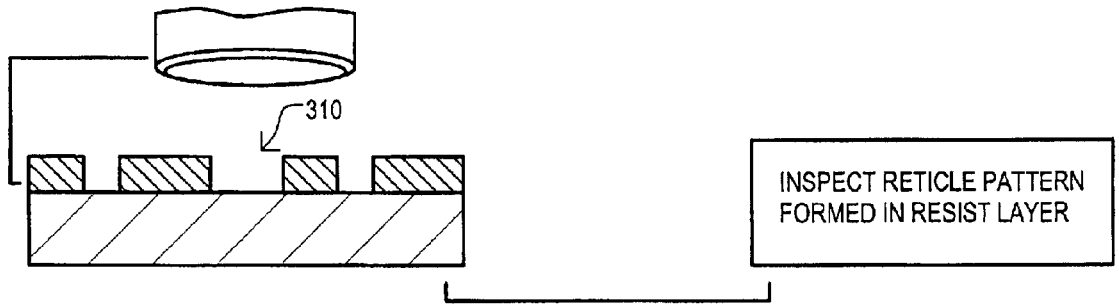

Referring now to FIG. 2E, following the formation of a reticle related pattern, a conformal conductive layers may be deposited on an etchable layer (step 210). Such a conformal conductive layer may be comprised of one or more layers. In the example of FIG. 2E, a conformal conductive layer may include two layers 210-0 and 210-11.

In one embodiment, layers (210-10 and 202-11) within a conformal conductive layer may both be formed from conductive materials. More particularly, a conformal layer may be an interconnect adhering layer that is included in an existing manufacturing process. Such an interconnect adhering layer may serve as an intermediate layer between a base material, such as a dielectric, and a conductive interconnect material, such as tungsten and/or aluminum that might not adhere as well to the underlying base material. Even more particularly, a layer 210-10 may comprise titanium (Ti), while a layer 210-11 may comprise titanium nitride (TiN).

A conformal layer may have a particular thickness. As but one example, a conformal layer may be no more than ½ of a minimum feature size. By way of example, in FIG. 2E, a feature 210-2 may be considered to be a minimum feature of size L. A total thickness of a conductive conformal layer (210-10 and 210-11) may be no more than ½L. Still further, a certain thickness may be advantageous for small feature sizes. Thus, a total conformal conductive thickness may be no more than about 1000 Å, more preferably no more than about 700 Å.

One particular embodiment may have a conformal conductive layer having a layer 210-10 comprised of about 400 Å of Ti, and a layer 210-11 comprised of about 300 Å of TiN.

Following the deposition of a conformal conductive layer, one or more etchable layers containing a reticle pattern may be inspected as described above. Namely, a wafer may be inspected for reticle-related defects using wafer inspection tools. A conformal layer may provide increased contrast of the patterned and non-patterned areas compared to the inspection of a resist pattern as described in the Background of the Invention.

Still further, in the event a defect is found, such a defect may then be verified further using a SEM. A conductive conformal layer may provide improved SEM inspection over conventional approaches, as conductive materials typically do not charge under an electron beam. In this way, an approach according to the present invention may be more advantageous over conventional approaches.

It is further noted that by increasing contrast in a pattern under inspection, the present invention may also allow an inspection system to use wafer auto-alignment features during the initial inspection setup. This can reduce human intervention and decrease overall examination time.

It is noted that while particular resist examples have been described, such resists may include positive or negative resists. Further, a photoresist system may also include an anti-reflective coating (ARC). Still further, and as noted above, a resist system may include a hard mask, as is well understood by those familiar with the art.

Along these same lines, while particular embodiments include a specific dielectric combination as an etchable layer, an etchable layer may be singular as noted. Further, the an etchable layer may be comprised of other materials, including but not limited to silicon nitride, borophosphosilicate glass (BPSG), thermally grown oxides, or spin-on glass (SOG), name but a few. Of course, patterning such a layer may include etching with a recipe/method particular to a given material.

It is further noted that a method of verification according to the present invention may be used on substrates other than those of a silicon wafer.

Still further, while the term "reticle" has used herein has described a piece of equipment that is exposed to light to form a pattern on an underlying material, a "reticle" may take alternate forms in different types of lithography. As but one example, e-beam, or other particle based systems may raster a beam across a pattern of resist. In such cases, a reticle may be in the form of data stored in such a machine that guides the rastering and/or activation of such beams.

Along these same lines, one skilled in the art would recognize that a reticle pattern might not be identical to a resulting resist pattern, or the like. More particularly, at smaller geometries a reticle pattern may include "hammerhead" type structures and/or notches that will not necessarily appear in a resulting developed pattern of photoresist. Such features can be used to overcome well know "corner effect" and the like.

Thus, while the preferred embodiments set forth herein have been described in detail, it should be understood that the present invention could be subject to various changes, substitutions, and alterations without departing from the spirit and scope of the invention. Accordingly, the present invention is intended to be limited only as defined by the appended claims.

What is claimed is:

1. A method of verifying a reticle, comprising the steps of:
providing a substrate having a uniform surface;
depositing a non-resist layer over the uniform surface of the substrate;
forming a layer of resist over the non-resist layer;
forming a reticle pattern in the layer of resist;
transferring the reticle pattern to the non-resist layer;
forming a conformal layer over the non-resist layer, wherein the non-resist layer includes a transferred reticle pattern, at least a portion of the transferred reticle pattern extending through the non-resist layer; and
inspecting the transferred reticle pattern for defects by comparing the transferred reticle pattern with a good reticle pattern.

2. The method of claim 1, wherein:
the conformal layer comprises a conductive material.

3. The method of claim 2, wherein:
the conformal layer comprises titanium.

4. The method of claim 3, wherein:
the conformal layer further comprises a plurality of stacked layers comprising a layer of titanium nitride formed over a layer of titanium.

5. The method of claim 2, wherein:
the transferred reticle pattern in the non-resist layer includes features having a minimum size L, and the conformal layer has a thickness of no more than ½L.

6. The method of claim 2, wherein:
the conformal layer has a thickness of no more than 1000 Å.

7. The method of claim 1, wherein:
the non-resist layer comprises silicon oxide.

8. The method of claim 7, wherein:
the non-resist layer comprises a layer of undoped silicon dioxide formed on a layer of phosphosilicate glass.

9. The method of claim 1, wherein:
the thickness of the non-resist layer is in the range of about 2500 Å to about 6000 Å.

10. The method of claim 1, wherein:
the thickness of the non-resist layer is at least 5000 Å.

11. The method of claim 1, wherein:
the uniform substrate comprises a silicon.

12. A method of verifying a reticle, comprising the steps of:
providing a substrate having a uniform surface;
depositing a non-resist layer over the uniform surface of the substrate;
forming a layer of resist over the non-resist layer;
forming a reticle pattern in the layer of resist;
transferring the reticle pattern to the non-resist layer;
forming a conductive conformal layer with a thickness of at least 100 Å over the transferred reticle pattern in the non-resist layer, at least a portion of a transferred reticle pattern extending through the non-resist layer; and
inspecting the reticle pattern in the deposited layer by comparing the transferred reticle pattern to a good reticle pattern.

13. The method of claim 12, wherein:
inspecting the transferred reticle pattern by means of automatic pattern inspection equipment.

14. The method of claim 13, wherein:
inspecting the transferred reticle pattern includes automatically aligning a wafer in the automatic pattern inspection equipment with the transferred reticle pattern formed in the non-resist layer.

15. The method of claim 12, wherein:
the transferred reticle pattern comprises a transferred contact reticle pattern.

16. The method of claim 12, further including:
the step of transferring the reticle pattern to the non-resist layer includes etching the non-resist layer, and
removing the patterned layer of resist.

17. A method, comprising the steps of:
providing a substrate having a uniform surface;
depositing a non-resist layer over the uniform surface of the substrate;
forming a layer of resist over the non-resist layer;
forming a reticle pattern in the layer of resist;
transferring the reticle pattern to the non-resist layer, at least a portion of the transferred reticle pattern extending through the non-resist layer;
forming a conformal layer over the non-resist layer to thereby increase contrast between patterned and non-patterned portions of the non-resist layer; and
inspecting the reticle patterned layer by comparing the transferred reticle pattern to a good reticle pattern.

18. The method of claim 17, wherein:
forming the non-resist layer comprises depositing a silicon oxide containing layer.

19. The method of claim 17, wherein:
the conformal layer is formed by depositing at least one conductive layer.

20. The method of claim 19, wherein:
the conformal layer further comprises an interconnect adhering layer.

* * * * *